(12) United States Patent
Jones

(10) Patent No.: US 10,279,111 B2
(45) Date of Patent: May 7, 2019

(54) APPARATUS AND KIT FOR PROVIDING PALLIATIVE CARE

(71) Applicant: Terry Parks Jones, Clemmons, NC (US)

(72) Inventor: Terry Parks Jones, Clemmons, NC (US)

( * ) Notice: Subject to any disclaimer, the term of this patent is extended or adjusted under 35 U.S.C. 154(b) by 205 days.

(21) Appl. No.: 13/904,102

(22) Filed: May 29, 2013

(65) Prior Publication Data
US 2014/0358059 A1 Dec. 4, 2014

(51) Int. Cl.
A61J 7/00 (2006.01)
A61M 37/00 (2006.01)
A61M 5/178 (2006.01)
A61J 1/06 (2006.01)

(52) U.S. Cl.
CPC .............. *A61M 5/178* (2013.01); *A61J 7/003* (2013.01); *A61J 7/0038* (2013.01); *A61M 37/00* (2013.01); *A61J 1/067* (2013.01)

(58) Field of Classification Search
CPC ........ A61M 37/00; A61M 5/178; A61F 13/38
See application file for complete search history.

(56) References Cited

U.S. PATENT DOCUMENTS

| 470,194 | A | | 3/1892 | Hosford | |
|---|---|---|---|---|---|
| 2,218,738 | A | * | 10/1940 | Boysen | A46B 5/00 132/320 |
| 3,324,855 | A | * | 6/1967 | Heimlich | A61B 17/02 401/133 |
| 4,747,719 | A | | 5/1988 | Parkin | |
| 4,795,421 | A | * | 1/1989 | Blasius et al. | 604/1 |
| 4,799,815 | A | | 1/1989 | Barabino et al. | |
| 5,158,532 | A | | 10/1992 | Peng et al. | |
| 5,830,186 | A | * | 11/1998 | Gonzales | A61M 31/00 604/131 |
| 6,238,213 | B1 | * | 5/2001 | Young | A61C 17/043 132/308 |
| 6,488,645 | B1 | | 12/2002 | Reinhard | |
| 7,008,392 | B2 | | 3/2006 | Beaudry | |
| 7,044,671 | B2 | * | 5/2006 | Parikh et al. | 401/183 |
| 7,789,845 | B1 | * | 9/2010 | Meliti | 604/1 |
| 2002/0108614 | A1 | * | 8/2002 | Schultz | 128/207.14 |
| 2005/0069373 | A1 | * | 3/2005 | Parikh | A46B 9/005 401/183 |
| 2008/0230408 | A1 | * | 9/2008 | Sogaro | A61M 35/006 206/222 |

* cited by examiner

Primary Examiner — Benjamin J Klein
Assistant Examiner — Sara A Sass
(74) Attorney, Agent, or Firm — Moore & Van Allen PLLC; W. Kevin Ransom

(57) ABSTRACT

Embodiments of the invention are directed to apparatuses and kits for providing palliative care. An exemplary apparatus comprises an elongate hollow shaft having a first and a second end. An absorbent material may be attached to the first end and the first end may be perforated such that the elongate hollow shaft may be filled with one or more liquid solutions that flow through the perforated end and disperse evenly throughout the absorbent material. A kit may additionally be provided for providing customized palliative care. The kit may comprise a means for injecting one or more liquid solutions into the elongate shaft. The kit may additionally comprise apparatuses that are prefilled with one or more liquid solutions.

9 Claims, 7 Drawing Sheets

PROVIDING A PALLIATIVE CARE APPARATUS, WHEREIN THE PALLIATIVE CARE APPARATUS COMPRISES AN ELONGATE SHAFT HAVING A FIRST AND A SECOND END, WHEREIN AN ABSORBENT MATERIAL IS ATTACHED TO THE FIRST END, WHEREIN THE FIRST END IS PERFORATED, AND WHEREIN THE SECOND END COMPRISES A GROOVE FOR FINGER PLACEMENT
702

↓

PROVIDING A MEASURED VOLUME OF AN EDIBLE LIQUID SOLUTION WITHIN THE ELONGATE SHAFT AND DISPERSED THROUGHOUT THE ABSORBENT MATERIAL, WHEREIN THE MEASURED VOLUME OF THE EDIBLE LIQUID SOLUTION IS A USER-SPECIFIC DOSAGE WHICH MAY AID IN PREVENTING A PATIENT FROM ASPIRATING
704

↓

INSERTING THE ABSORBENT MATERIAL, ATTACHED TO THE FIRST END OF THE HOLLOW SHAFT, INTO THE MOUTH OF THE PATIENT SUCH THAT THE EDIBLE LIQUID SOLUTION MAY BE CONSUMED BY THE PATIENT
706

FIG. 7

APPARATUS AND KIT FOR PROVIDING PALLIATIVE CARE

BACKGROUND

Typically, patients who are unable to eat, drink, or safely swallow due to surgery, breathing machines, such as ventilators, or other medical reasons are presented with limited options for palliative care. Currently palliative care for patients with these conditions is limited to the use of lemon glycerin swabs or ice chips. The lemon glycerin swabs may additionally be used as a temporary alternative for oral hygiene. However, the use of lemon discouraged by many health professionals because of the drying solutions in lemon glycerin swabs. In particular, according to the American Dental Hygienist's Association, the Lemon glycerin swabs may result in decalcification of patient's teeth. Furthermore, the lemon glycerin swabs do not offer the patients a variety of flavors, and can be very tiresome when this is the only option that patients are presented with.

Therefore, a need exist for a customized palliative care apparatus, where patients may choose the types of flavors in which they are given with the use of the swab. Such an apparatus may offer an alternative choice for comfort and care to people with similar health problems. It may also expand the flavor options for patients that are terminally ill versus being limited to the flavor of lemon when they cannot eat.

BRIEF SUMMARY

Embodiments of the invention are directed to methods, apparatuses and kits for providing palliative care to patients. The method may comprise several steps such for providing palliative care to patients. A palliative care apparatus is provided which comprises an elongate hollow shaft having a first and a second end. An absorbent material is attached to the first end, and the first end is perforated. A volume of liquid solution is then measured, and the palliative care apparatus is filled with the measure volume of liquid solution. The volume of liquid solution is a user-specific dosage which prevents a patient from aspirating. The first end of the hollow shaft may then be inserted into the mouth of the patient.

The apparatus may comprise an elongate hollow shaft having a first and a second end. An absorbent material may be attached to the first end, and the first end may be additionally perforated. In some embodiments, the first end is punctured such that it comprises one or more holes. In such an embodiment, the one or more holes may vary in size. In some embodiments, the elongate hollow shaft is filled with a liquid solution. The liquid solution may flow through the one or more holes such that it is dispersed evenly throughout the absorbent material. In some embodiments, the elongate hollow shaft is filled with a liquid solution that is injected into the elongate hollow shaft through the second end. In some embodiments, the second end of the apparatus may comprise a one-way valve. The one-way valve may be positioned such that the liquid solution flows towards the first end. In other embodiments, the elongate hollow shaft may comprise a flexible outer container having a fragile container stored therein. The fragile container may additionally have a liquid solution stored therein. In such an embodiment, the flexible outer container may be bent such that the fragile container breaks and releases the liquid solution into the elongate hollow shaft. In some embodiments, the elongate shaft of the apparatus may be filled with a liquid solution and the first end may comprise a dripping mechanism.

A kit for palliative care may also be provided. The kit may comprise a portable housing storing a plurality of components for palliative care. In some embodiments, the components may include one or more elongate hollow shafts having a first and a second end. The absorbent material may be attached to the first end and wherein the first end may be perforated. The kit may additionally comprise one or more liquid solutions and one or more liquid injection devices. The one or more liquid injection devices may be used to inject the one or more liquid solution into the second end of the elongate hollow shaft. In some embodiments, the liquid injection device may be a syringe. In some embodiments, the liquid injection device may be a twist-off capsule having the one or more liquid solution stored therein. In other embodiments, the one or more elongate hollow shafts are prefilled with the one or more liquid solutions. In some embodiments, the one or more elongate hollow shafts comprise a flexible outer container having a fragile container stored therein. The fragile container may have the one or more liquid solutions stored therein. In such an embodiment, the flexible outer container may be bent such that the fragile container breaks and releases the one or more liquid solutions into the one or more elongate hollow shaft. In some embodiments, the one or more liquid solutions are stored in a perforated blister package having one or more individual compartments. The one or more individual compartments may be removed from the perforated blister package. In some embodiments, the one or more liquid solutions may be stored in one or more disposable packages.

For patients who crave water, a favorite dessert and/or food, such as pureed fruits or chocolate, the apparatus may offer pleasure through taste and smell, rather than a sufficient number of calories in terminally ill patients. Users may inject personalized flavors into the apparatus or choose from a selection of prepackaged flavors.

BRIEF DESCRIPTION OF THE DRAWINGS

Figure 1:
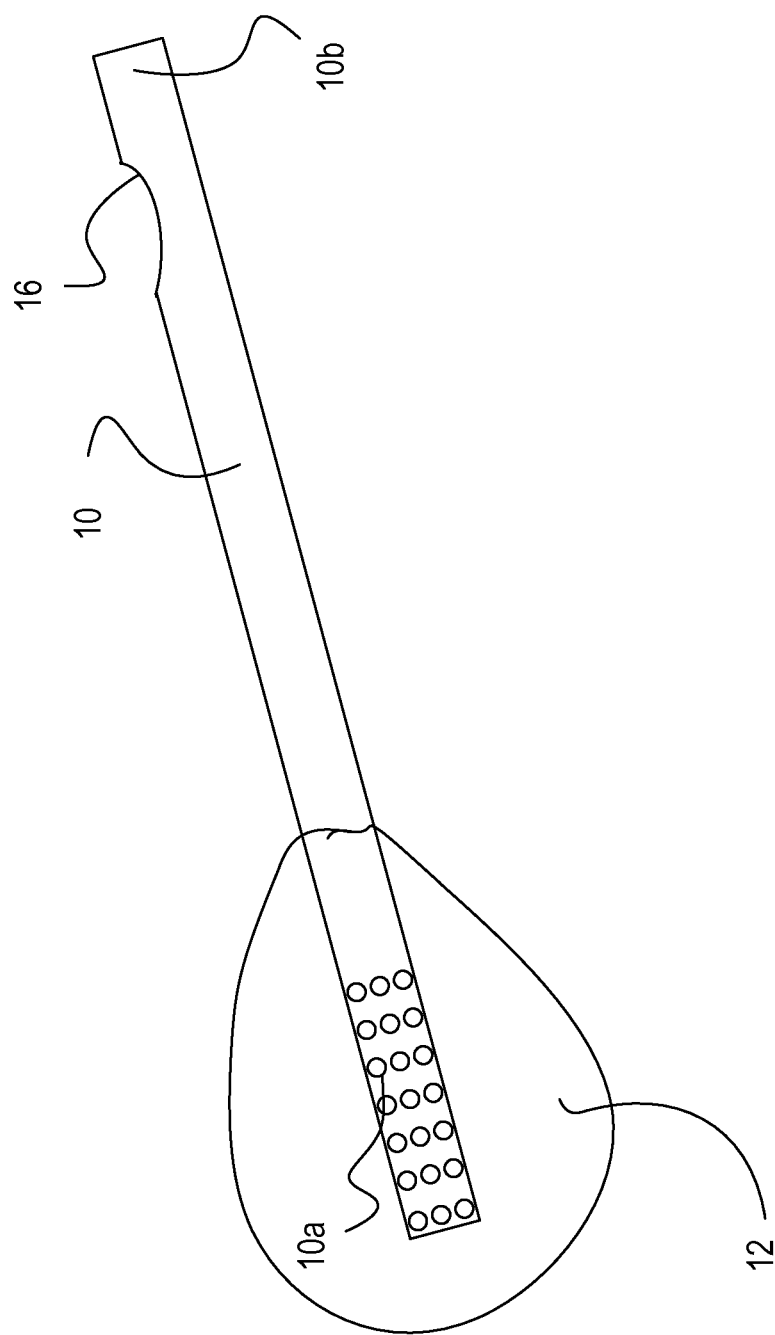
Figure 2A:
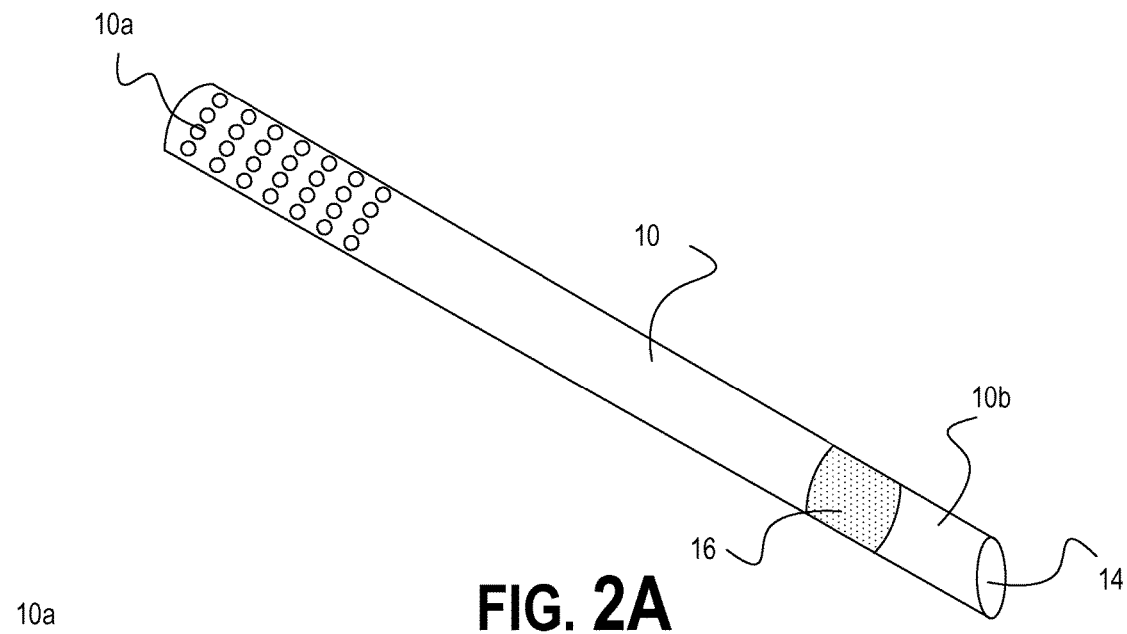
Figure 2B:
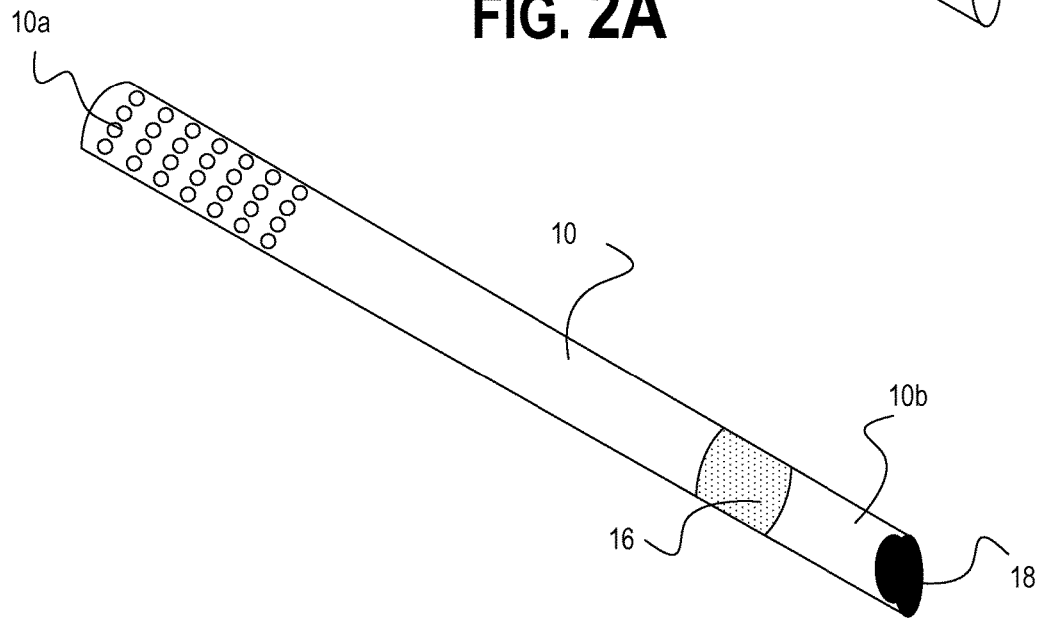
Figure 2C:
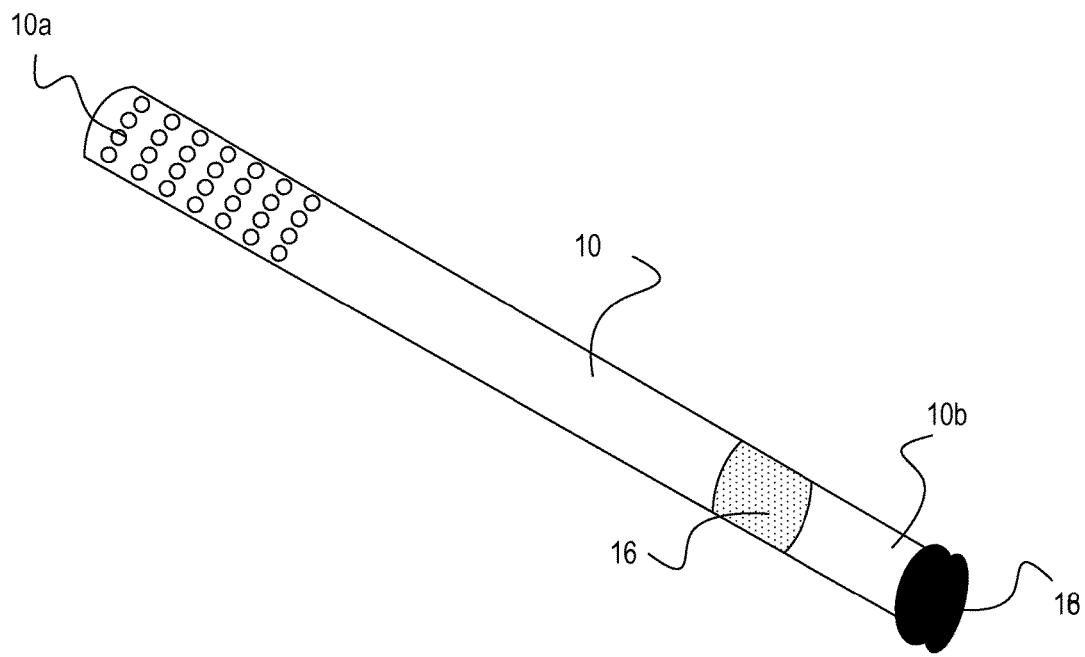
Figure 3:
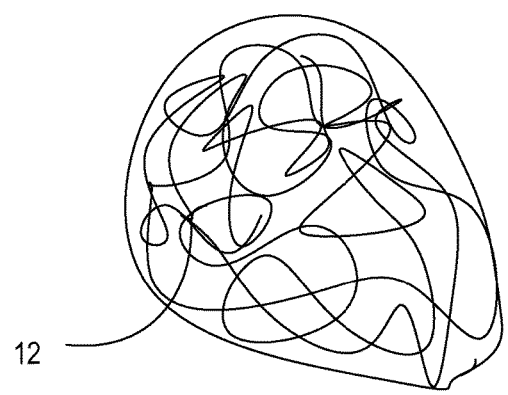
Figure 4:
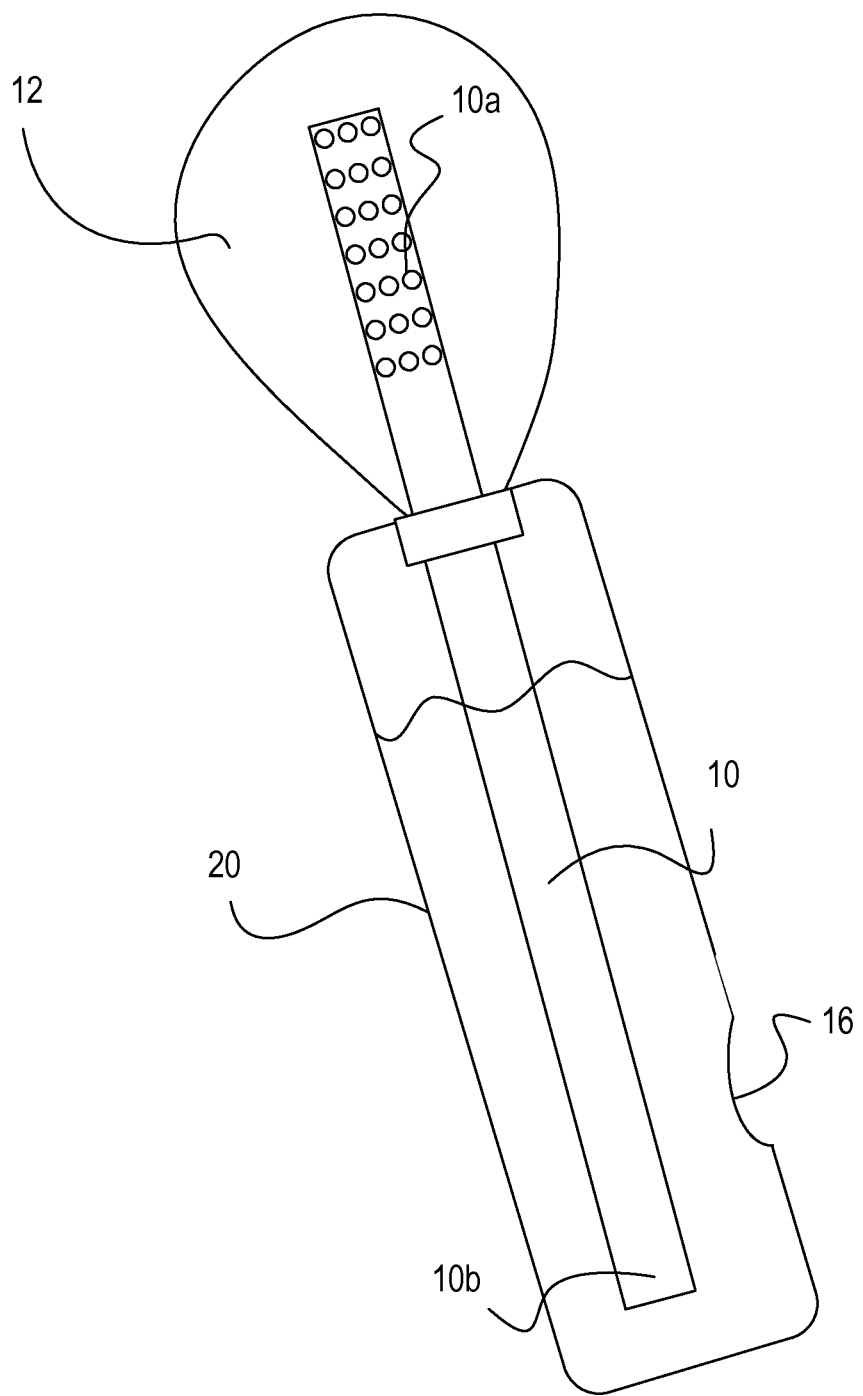
Figure 5A:
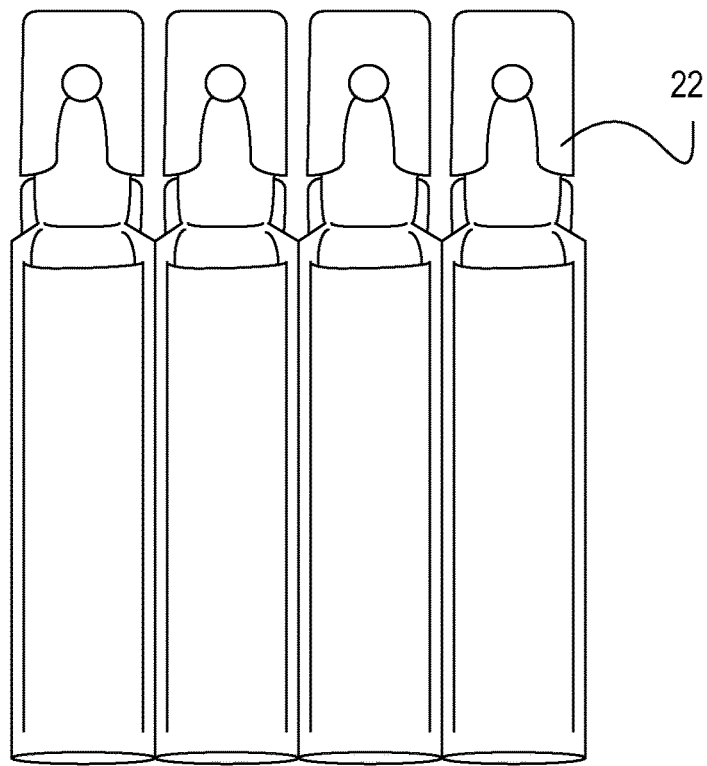
Figure 5B:
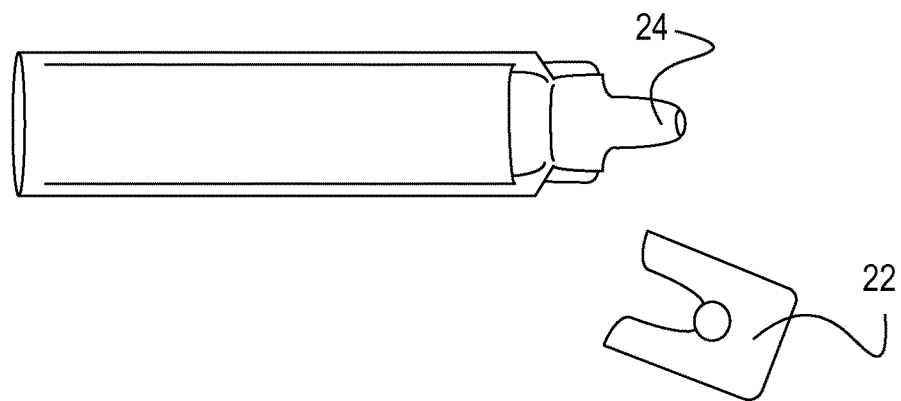
Figure 6:
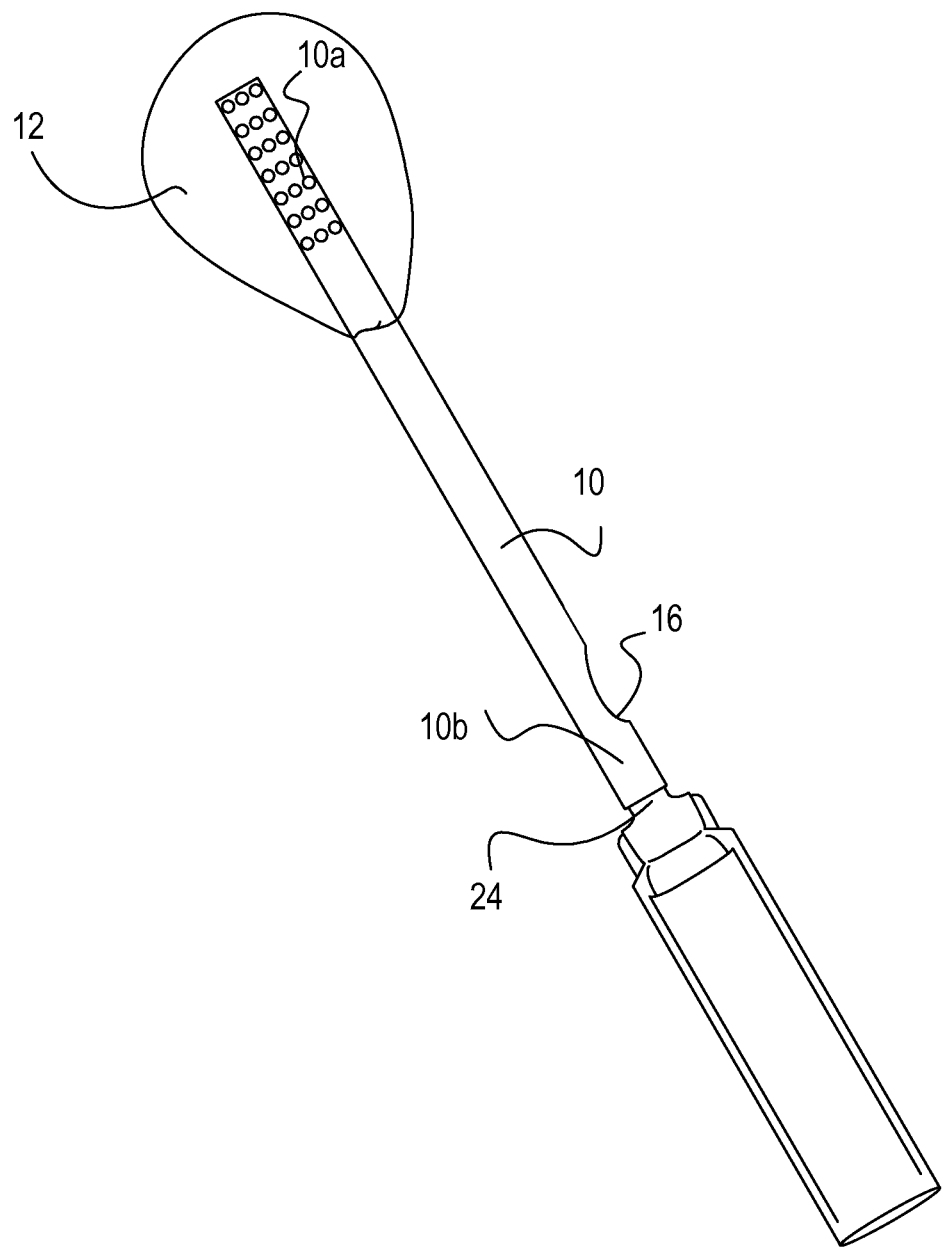

Having thus described embodiments of the invention in general terms, reference will now be made to the accompanying drawings, where:

FIG. 1 illustrates an apparatus for providing palliative care, in accordance with embodiments of the present invention;

FIG. 2A illustrates an elongate hollow shaft of an apparatus for providing palliative care, in accordance with embodiments of the present invention;

FIG. 2B illustrates an elongate hollow shaft of an apparatus for providing palliative care, in accordance with embodiments of the present invention;

FIG. 2C illustrates an elongate hollow shaft of an apparatus for providing palliative care, in accordance with embodiments of the present invention;

FIG. 3 illustrates an absorbent material of an apparatus for providing palliative care, in accordance with embodiments of the present invention;

FIG. 4 illustrates an apparatus for providing palliative care removably coupled with a reservoir, in accordance with embodiments of the present invention;

FIG. 5A illustrates an liquid injection device, in accordance with embodiments of the present invention;

FIG. 5B illustrates an liquid injection device, in accordance with embodiments of the present invention;

FIG. 6 illustrates an apparatus for providing palliative care removably coupled with a liquid injection device, in accordance with embodiments of the present invention; and FIG. 7 provides a flow diagram illustrating a method for providing palliative care, in accordance with embodiments of the present invention.

DETAILED DESCRIPTION OF EMBODIMENTS OF THE INVENTION

Embodiments of the present invention now may be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Embodiments of the invention are directed towards apparatuses and kits for providing palliative care. The invention enables a user to soothe and refresh dry mouths of patients by restricting oral intake with the use of a customized apparatus for providing palliative care. The apparatus may be customized on a patient-to-patient basis using a plurality of components contained within a palliative care kit. Referring now to FIG. 1, FIG. 1 illustrates an apparatus for providing palliative care, according to embodiments of the present invention. The apparatus comprises an elongate hollow shaft 10 having a first and second end 10a, 10b, respectively, and an absorbent material 12 attached to at least one end of the shaft 10. The apparatus may additionally comprise a groove 16 for finger placement.

The groove 16 may be ergonomically designed such that it allows for the natural placement of a finger of either the patient or a caregiver while utilizing the apparatus. The groove 16, as illustrated in FIG. 2, may be of a different texture from the rest of the apparatus such that the groove itself can be differentiated based on texture, and independent of sight.

Referring now to FIG. 2, composed of FIGS. 2A, 2B, and 2C, FIG. 2 illustrates an elongate hollow shaft 10, according to embodiments of the invention. At least one end of the shaft 10 contains an opening 14 to the hollow interior of the shaft 10. In the illustrated embodiments, the second end 10b of the shaft 10 contains an opening 14 to interior of the shaft 10. The elongate hollow shaft 10 is capable of housing a liquid solution within the interior of the shaft. In an exemplary embodiment, the elongate hollow shaft inserting the absorbent material attached to the first end of the hollow shaft into the mouth of the patient such that the edible liquid solution may be consumed by the shaft 10 is filled with an edible liquid solution that may be consumed by a human being. In some embodiments, the liquid solution may be injected into the opening 14 of the shaft 10. The elongate hollow shaft 10 may be filled with a plurality of liquid solutions. In an alternate embodiment, the elongate hollow shaft 10 is prefilled with one or more liquid solutions. In some embodiments, the shaft 10 may be filled with a combination of liquid solutions. Liquid solutions used to fill the shaft 10 may include, but not be limited to, glycerin based liquids, juices, water, melted chocolate, and/or any combination of the aforementioned liquids. In some embodiments, the liquid solution may be a liquid or gel. In other embodiments, the liquid solution may be frozen within the elongate hollow shaft 10 and/or the absorbent material 12. In such an embodiment, the elongate hollow shaft 10 is additionally capable of housing a solid within the interior of the shaft. For example, a liquid solution may be injected into the opening 14 of the shaft 10, upon freezing the apparatus the liquid solution may be converted to a solid within the shaft 10 and/or the absorbent material 12.

As such, the apparatus may additionally comprise a cap 18 for enclosing the opening 14 to ensure the liquid solution remains within the shaft 10. In some embodiments, as illustrated in FIG. 2B, the cap 18 may be a plug that at least partially extends throughout the interior of the second end 10b of the shaft 10 such that it completely encloses the opening 14 of the shaft 10. In other embodiments, as illustrated in FIG. 2C, the cap 18 may extend around the perimeter of the second end 10b of the shaft 10 such that is completely encloses the opening 14 of the shaft 10. In some embodiments, the cap 18 may be a combination of the caps illustrated in FIGS. 2B and 2C. To this extent, the cap 18 may at least partially extend throughout the interior and around the perimeter of the second end 10b such that is completely encloses the opening 14 of the shaft 10.

In some embodiments at least one end of the elongate hollow shaft 10 comprises a one-way valve. The one-way valve may be positioned such that a liquid solution can flow through the valve into the shaft 10 but not be able to exit the shaft through the valve. In an exemplary embodiment, the one-way valve may be located at the opening 14 of the shaft 10 and the liquid solution may flow from the second end 10b towards the first end 10a. In some embodiments, the elongate hollow shaft 10 comprises a flexible outer container having a fragile container stored therein. The fragile container may have a liquid solutions stored therein such that when the flexible outer container is bent the fragile container breaks and releases the liquid solutions into the interior of the shaft 10. In some embodiments, at least one end of the shaft 10 comprises a dripping mechanism to control rate at which the liquid solution exits the shaft 10. In an exemplary embodiment, the first end 10a of the elongate hollow shaft 10 comprises a dripping mechanism such that the rate at which the liquid solutions exits the shaft 10, through the one or more holes, may be altered based upon the properties of the dripping mechanism.

At least one end of the elongate hollow shaft 10 is punctured such that it comprises one or more holes. In an exemplary embodiment, the first end 10a of the shaft 10 is punctured such that it comprises a plurality of holes. The one or more holes may vary in size and/or shape. In some embodiments, as shown in FIGS. 1 and 2, the size and shape of the plurality of holes is consistent. In alternate embodiments, at least one hole is a different size and/or shape from at least one other hole punctured in the shaft 10. As illustrated in FIG. 1, the elongate hollow shaft 10 defines a longitudinal axis on which the absorbent material 12 is attached. In an exemplary embodiment, at least one end of shaft 10, having a plurality of holes punctured therein, extends at least partially through the absorbent material 12 such that the plurality of holes punctured are completely covered by the absorbent material 12. In an exemplary embodiment, the liquid solution housed within the elongate hollow shaft 10 flows from the second end 10b to the first end 10a such that it exits the shaft 10 through the one or more holes punctured within the first end 10a, and is evenly dispersed throughout the absorbent material 12.

The elongate hollow shaft 10 may be formed of any suitable, durable and relatively rigid material such as wood, paper, aluminum, plastic, and/or the like. In an exemplary embodiment, the elongate hollow shaft 10 is formed of plastic. The length, shape, and/or size of the elongate hollow shaft 10 may vary according to its particular use. In an exemplary embodiment, the elongate hollow shaft 10 may be 4 inches long with a diameter of 0.5 centimeters. To this extent, the hollow interior may be wide enough to allow a liquid to easily flow within the shaft 10.

Referring now to FIG. 3, FIG. 3 illustrates a swab pouch comprised of at least one absorbent material 12, according to embodiments of the invention. In some embodiments, the absorbent material 12 is attached to the at least one end of the shaft 10 with the use of an adhesive. In an exemplary embodiment, the absorbent material 12 is attached to the first end 10a of the shaft 10, as illustrated in FIG. 1. The absorbent material 12 may be any fibrous material capable of absorbing a liquid that may be housed within the interior of the shaft 10. The absorbent material 12 may include, but not be limited to, materials such as cotton, polyester, rayon, foam, or any combination of the aforementioned materials.

Referring now to FIG. 4, FIG. 4 illustrates a palliative care apparatus in conjunction with a reservoir. As illustrated, in some embodiments, the palliative care apparatus may be removably coupled with a reservoir 20. The reservoir 20 may be additionally filled with one or more liquid solutions. The elongate hollow shaft 10 may be at least partially encompassed by the reservoir 20 such that at least one end of the elongate hollow shaft 10 is partially submerged into the liquid solution contained therein. As such, the groove 16 may be located on the reservoir 20 in addition to or in alternative to being located on the shaft 10. To this extent, the liquid solution contained within the apparatus may flow from the reservoir 20 into the elongate hollow shaft 10 and out the one or more holes, and be evenly dispersed throughout the absorbent material 12. In some embodiments, by applying pressure to the reservoir 20, the liquid solution stored therein may be injected into the interior of the shaft 10. In some embodiments the apparatus may be removably coupled with the reservoir 20 by means of adhesive. In other embodiments, the apparatus may be mechanically coupled with the reservoir 20. For example, at least a portion of the elongate hollow shaft 10 may comprise ridges and the reservoir may comprise complimentary ridging such that the apparatus may be screwed into the reservoir.

In further embodiments of the invention, a palliative care kit may be provided. The kit may comprise a portable housing device for storing a plurality of components for palliative care. Components of the palliative care kit may include, but not be limited to, one or more elongate hollow shafts 10 having a first and second end 10a, 10b, respectively, and an absorbent material 12 attached to at least one end of the shaft 10, one or more liquid solutions, and one or more liquid injection devices. In some embodiments, for sanitation purposes, the one or more elongate hollow shafts 10 having a first and second end 10a, 10b, respectively, and an absorbent material 12 attached to at least one end of the shaft 10, are stored within a separate package prior to being placed within the palliative care kit. For example, the one or more elongate hollow shafts 10 having a first and second end 10a, 10b, respectively, and an absorbent material 12 attached to at least one end of the shaft 10, may be stored in a foil package prior to being placed within the palliative care kit.

In some embodiments, the one or more liquid injection devices may be used to inject the one or more liquid solutions into the second end 10b of the elongate hollow shaft 10. As illustrated in FIGS. 5A and 5B, the liquid injection device may be a twist-off capsule having the one or more liquid solutions stored therein. In such an embodiment, the twist-off cap 22 can be removed such that the tip 24 of the capsule may be inserted into the opening 14 of the shaft 10. By applying pressure to the twist-off capsule, the liquid solution stored therein is injected into the interior of the shaft 10. In such an embodiment, the tip 24 of the twist-off capsule may be smaller than the diameter of the shaft 10 such that it can be easily inserted into the opening 14. In some embodiments, as illustrated in FIG. 4A, the palliative care kit may contain a plurality of twist-off capsules that are temporarily attached to one another and may be separated on an independent usage basis. In some embodiments, the plurality of twist-off capsules may contain the same liquid solution. In alternate embodiments, the plurality of twist-off capsules may contain the different liquid solutions.

Referring now to FIG. 6, FIG. 6 illustrates a palliative care apparatus in conjunction with a liquid injection device. As illustrated, in some embodiments, the palliative care apparatus may be removably coupled with a twist-off capsule. The twist-off capsule may be at least partially encompassed by the elongate hollow shaft 10. To this extent, the liquid solution contained within the apparatus may flow from the twist-off capsule into the elongate hollow shaft 10 and out the one or more holes, and be evenly dispersed throughout the absorbent material 12. In some embodiments the apparatus may be removably coupled with the twist-off capsule by means of adhesive. In other embodiments, the apparatus may be mechanically coupled with the twist-off capsule. For example, at least a portion of the interior of the elongate hollow shaft 10 may comprise ridges and the exterior of the tip 24 of the twist-off capsule may comprise complimentary ridging such that the twist-off capsule may be screwed into at least one end of the shaft 10.

In some embodiments, the liquid solutions may be stored in one or more disposable packages. In an exemplary embodiment, the liquid solutions are stored in a perforated blister package having one or more individual compartments such that the individual compartments can be removed from the perforated blister package. The perforated blister package may be covered with foil, plastic, and/or the like. In such an embodiment, the liquid injection device may be a syringe that is used to remove the liquid solution from the individual compartment and inject the solution into the opening 14 of the shaft 10. In some embodiments, the perforated blister package may comprise a built in mechanism which is capable of injecting a liquid solution into the elongate shaft. For example, the built in mechanism may be a plurality of channels or tubes that extend from the reservoirs of the perforated blister packages and are capable of being inserted into the elongate shaft such that the liquid is injected from the perforated blister package into at least one end of the elongate shaft 10.

In some embodiments, the liquid solutions may be stored in one or more tear drop shaped capsules. In one embodiment, the tear drop shaped capsules may be punctured such that the liquid solution is released into the elongate hollow shaft. In yet another embodiment, the tear drop shaped capsule may release the liquid solution when pressure is applied to the capsule. The kit may additionally comprise a dissolvable strip composed of a customized flavor. In some embodiments, the dissolvable strip may be comprised of edible food starch that is saturated with a plurality of flavors.

Referring now to FIG. 7, a method for providing palliative care is provided. At step 702 the method comprises providing a palliative care apparatus. In some embodiments, the palliative care apparatus comprises an elongate hollow shaft having a first and a second end. The palliative care apparatus may additionally comprise an absorbent material is attached to the first end, and wherein the first end is perforated. The second end may comprise a groove for finger placement. At step 704, the method comprises providing a measured volume of liquid solution. In specific embodiments, the measured volume of liquid solution is a user-specific dosage which may aid in preventing a patient from aspirating. For example, in some embodiments, the measured volume of liquid solution is between 0.375 mL and 0.625 mL. The edible liquid solution may be stored within the elongate shaft and dispersed throughout the absorbent material. In some embodiments, the method further comprises filling the palliative care apparatus with the measured volume of liquid solution. In some embodiments the liquid solution is impregnated into the device such that it flows through the first end and is dispersed evenly throughout the absorbent material. At step 706, the method comprises inserting the first end of the hollow shaft into the mouth of the patient. After filling the palliative care apparatus with the liquid solution, the method may further comprise freezing the palliative care apparatus.

Although many embodiments of the present invention have just been described above, the present invention may be embodied in many different forms and should not be construed as limited to the embodiments set forth herein; rather, these embodiments are provided so that this disclosure will satisfy applicable legal requirements. Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. Accordingly, the terms "a" and/or "an" shall mean "one or more," even though the phrase "one or more" is also used herein. Like numbers refer to like elements throughout.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations, modifications, and combinations of the just described embodiments can be configured without departing from the scope and spirit of the invention. Therefore, it is to be understood that, within the scope of the appended claims, the invention may be practiced other than as specifically described herein.

What is claimed is:

1. An apparatus for providing palliative care, the apparatus comprising:
    an elongate shaft having a body extending between a first and a second end, wherein said body of said elongate shaft has a hollow portion extending from the first end toward the second end, wherein the hollow portion extends completely through the elongate shaft, wherein the shaft adjacent to the first end is perforated with two or more holes located on an outer surface of the body of said elongate shaft adjacent to the first end, the hollow portion being in fluid communication with the holes such that the holes open into the hollow portion of said elongate shaft, and wherein the second end comprises a groove, the groove being defined by a curved concave surface located in the outer surface of the body of the elongate shaft adjacent to the second end of the body of the elongate shaft over the hollow portion of the body of the elongate shaft, wherein the curved concave surface extends from the second end of the body of the elongate shaft toward the first end of the body of the elongate shaft, wherein the groove is configured for receiving on the curved concave surface a finger of a user so that the user may grip said elongate shaft via placement of the user's finger on the curved concave surface; and
    an absorbent material attached to the first end of said elongate shaft, wherein the first end of the elongate shaft extends at least partially through the absorbent material such that the two or more holes located on the outer surface of the body of said elongate shaft are covered by the absorbent material and centralized within the absorbent material,
    wherein an edible liquid solution may be introduced into the hollow portion of the elongate shaft and flow from the hollow portion into the two or more holes located on the outer surface of the body of said elongate shaft adjacent to the first end of the body of the elongate shaft and into the absorbent material located on the first end of said elongate shaft for oral delivery to a user via the absorbent material.

2. The apparatus of claim 1, the two or more holes located at the first end of said elongate shaft are of different sizes.

3. The apparatus of claim 1, wherein the groove has an outer surface texture that is different from a texture of said elongate shaft.

4. The apparatus of claim 1 further comprising a reservoir coupled to the second end of said shaft for maintaining the edible liquid solution, the reservoir being separate from the absorbent material attached to the first end of said shaft.

5. The apparatus of claim 1, wherein the first end of said elongate shaft is open to the hollow portion of the body and second end of said elongate shaft is closed.

6. The apparatus of claim 5, wherein the elongate hollow shaft is filled with an edible liquid solution.

7. The apparatus of claim 5, wherein the second end comprises a one-way valve configured to receive an edible solution.

8. The apparatus of claim 1, wherein the second end comprises an injection device for injecting an edible liquid solution into the elongate hollow shaft.

9. The apparatus of claim 1 further comprising a flexible outer container connected to the second end of said elongated shaft, and a fragile container located in the flexible outer container comprising an edible liquid solution stored therein, and wherein the flexible outer container may be bent such that the fragile container breaks and releases the edible liquid solution into the elongate hollow shaft.

* * * * *